(12) United States Patent
Karlsson et al.

(10) Patent No.: US 8,152,766 B2
(45) Date of Patent: Apr. 10, 2012

(54) DEVICE FOR DELIVERING MEDICAMENT ENCOMPASSING A PRESSURE RELEASE MECHANISM

(75) Inventors: Anders Karlsson, Saltsjöbaden (SE); Stefan Högdahl, Stockholm (SE)

(73) Assignee: SHL Group AB, Nacka Strand (SE)

( * ) Notice: Subject to any disclaimer, the term of this patent is extended or adjusted under 35 U.S.C. 154(b) by 304 days.

(21) Appl. No.: 12/375,085

(22) PCT Filed: Aug. 15, 2007

(86) PCT No.: PCT/EP2007/058428
§ 371 (c)(1),
(2), (4) Date: Jan. 26, 2009

(87) PCT Pub. No.: WO2008/020023
PCT Pub. Date: Feb. 21, 2008

(65) Prior Publication Data
US 2009/0281495 A1 Nov. 12, 2009

(30) Foreign Application Priority Data
Aug. 18, 2006 (SE) ...................................... 0601705

(51) Int. Cl.
*A61M 5/20* (2006.01)
(52) U.S. Cl. ....................................... 604/134; 604/133
(58) Field of Classification Search .......... 604/131–136, 604/218, 223–224, 228–229, 202–204, 206–214, 604/225
See application file for complete search history.

(56) References Cited

U.S. PATENT DOCUMENTS

| | | | | |
|---|---|---|---|---|
| 4,413,760 A | * | 11/1983 | Paton | 222/309 |
| 4,883,472 A | * | 11/1989 | Michel | 604/208 |
| 5,370,629 A | * | 12/1994 | Michel et al. | 604/207 |
| 5,626,566 A | * | 5/1997 | Petersen et al. | 604/208 |
| 5,820,602 A | * | 10/1998 | Kovelman et al. | 604/187 |
| 6,371,939 B2 | * | 4/2002 | Bergens et al. | 604/156 |
| 6,899,698 B2 | * | 5/2005 | Sams | 604/211 |
| 7,678,085 B2 | * | 3/2010 | Graf | 604/187 |
| 2003/0160072 A1 | * | 8/2003 | Geiser et al. | 222/327 |
| 2004/0143224 A1 | | 7/2004 | Field et al. | |
| 2006/0276753 A1 | * | 12/2006 | Kronestedt et al. | 604/186 |
| 2008/0051712 A1 | * | 2/2008 | Fiechter et al. | 604/134 |

FOREIGN PATENT DOCUMENTS

| | | |
|---|---|---|
| EP | 1728529 A1 | 12/2006 |
| GB | 2 142 245 A | 1/1985 |
| WO | 2005/079886 A3 | 9/2005 |

OTHER PUBLICATIONS

PCT International Search Report, mailed Dec. 18, 2007, in connection with International Application No. PCT/EP2007/058428.
PCT Written Opinion, mailed Dec. 18, 2007, in connection with International Application No. PCT/EP2007/058428.

* cited by examiner

*Primary Examiner* — Nicholas Lucchesi
*Assistant Examiner* — Melissa A Snyder
(74) *Attorney, Agent, or Firm* — Potomac Patent Group PLLC

(57) ABSTRACT

The present invention relates to a device for delivering medicament, comprising a container (12) arranged to contain medicament, which container further comprises an opening arranged to expel medicament from the container, pressure means (16, 18) arranged to exert pressure on the medicament inside the container (12) for expelling a certain predetermined quantity of the medicament through the opening, driving means (26, 42) for driving said pressure means (16, 18), and activation means (46) for activating said driving means (26, 42) wherein said device comprises pressure release means (20) which are adapted, arranged and designed such that, when the predetermined dose has been expelled through the opening, the pressure on the medicament is released.

11 Claims, 5 Drawing Sheets

[Fig. 1]

[Fig. 3a]
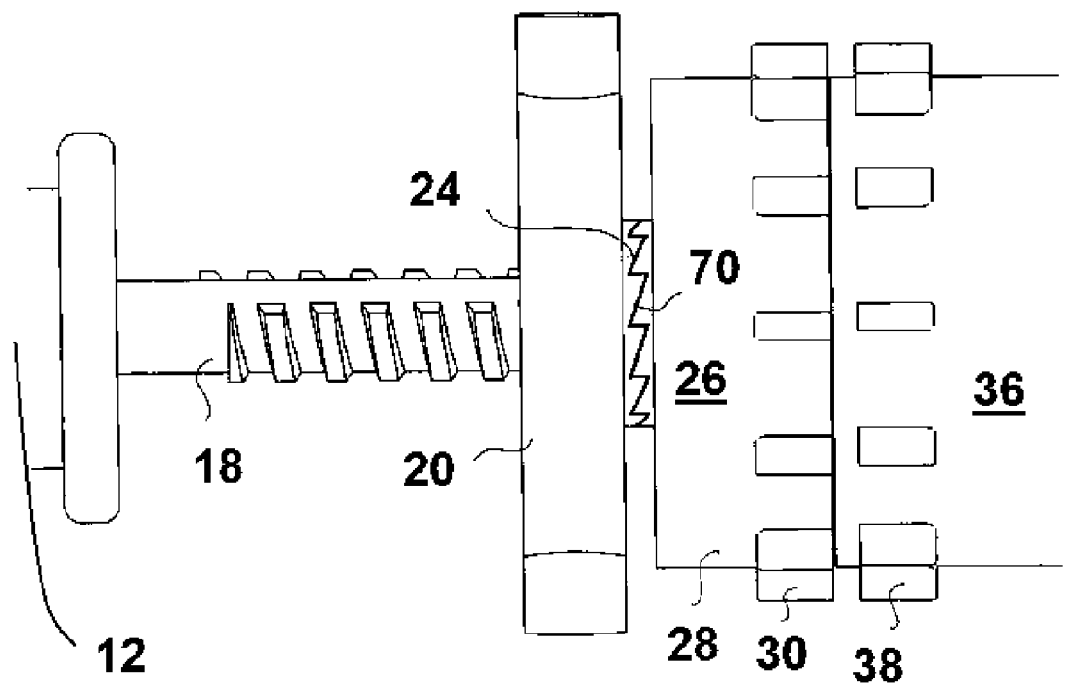
[Fig. 3b]
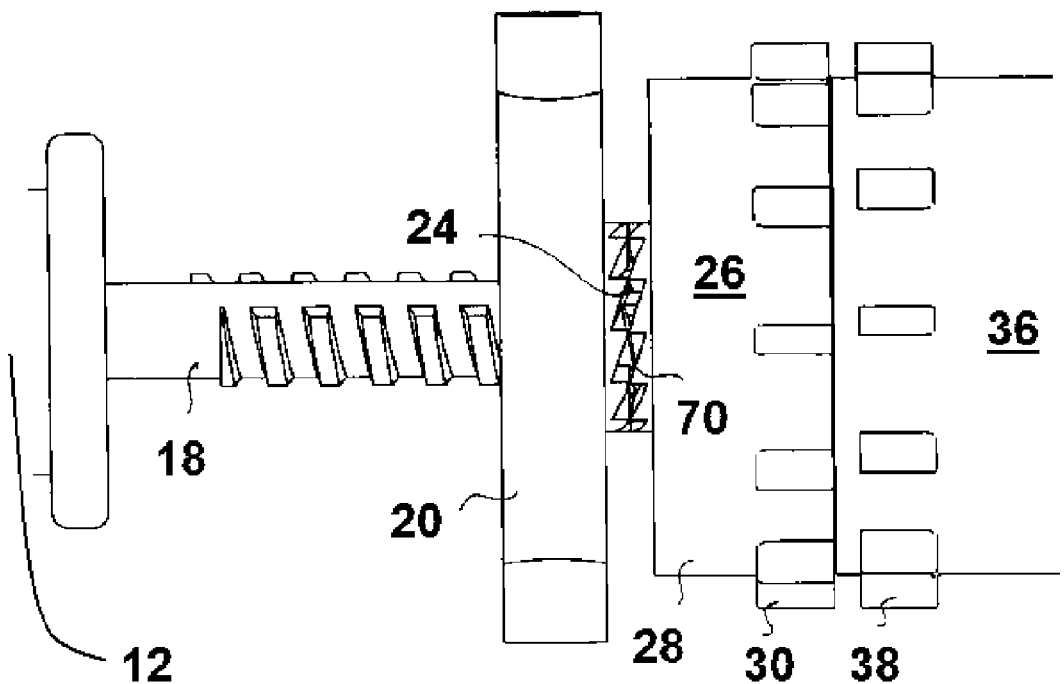

[Fig. 4a]
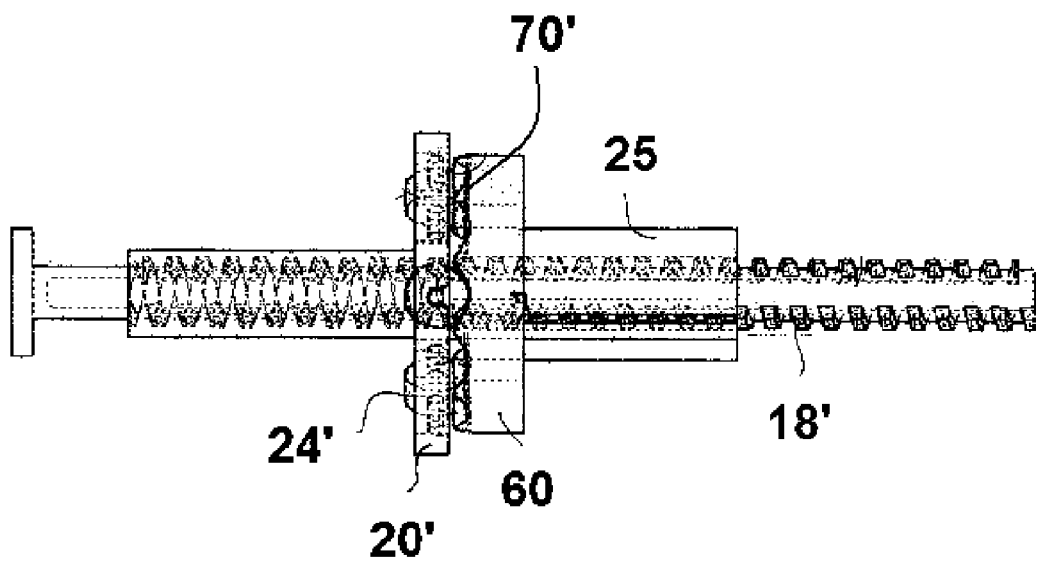
[Fig. 4b]
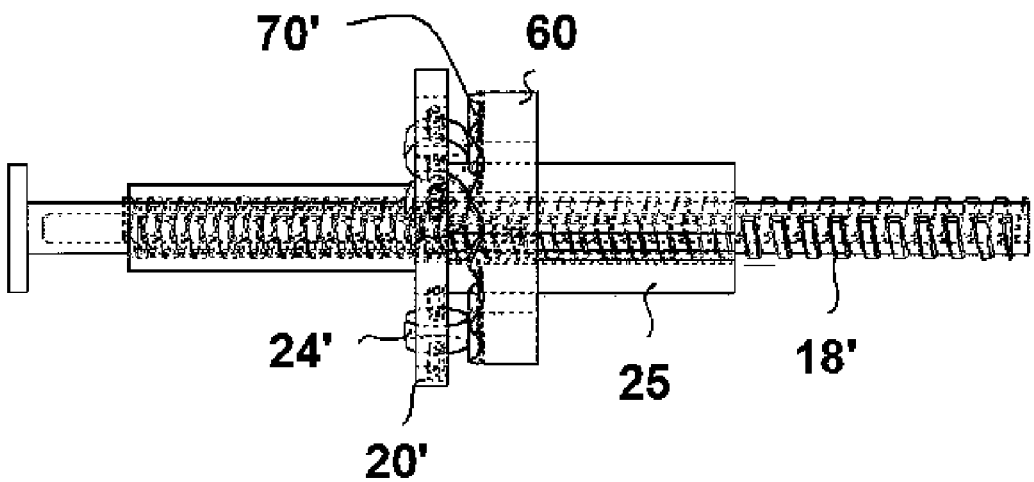

[Fig. 5]
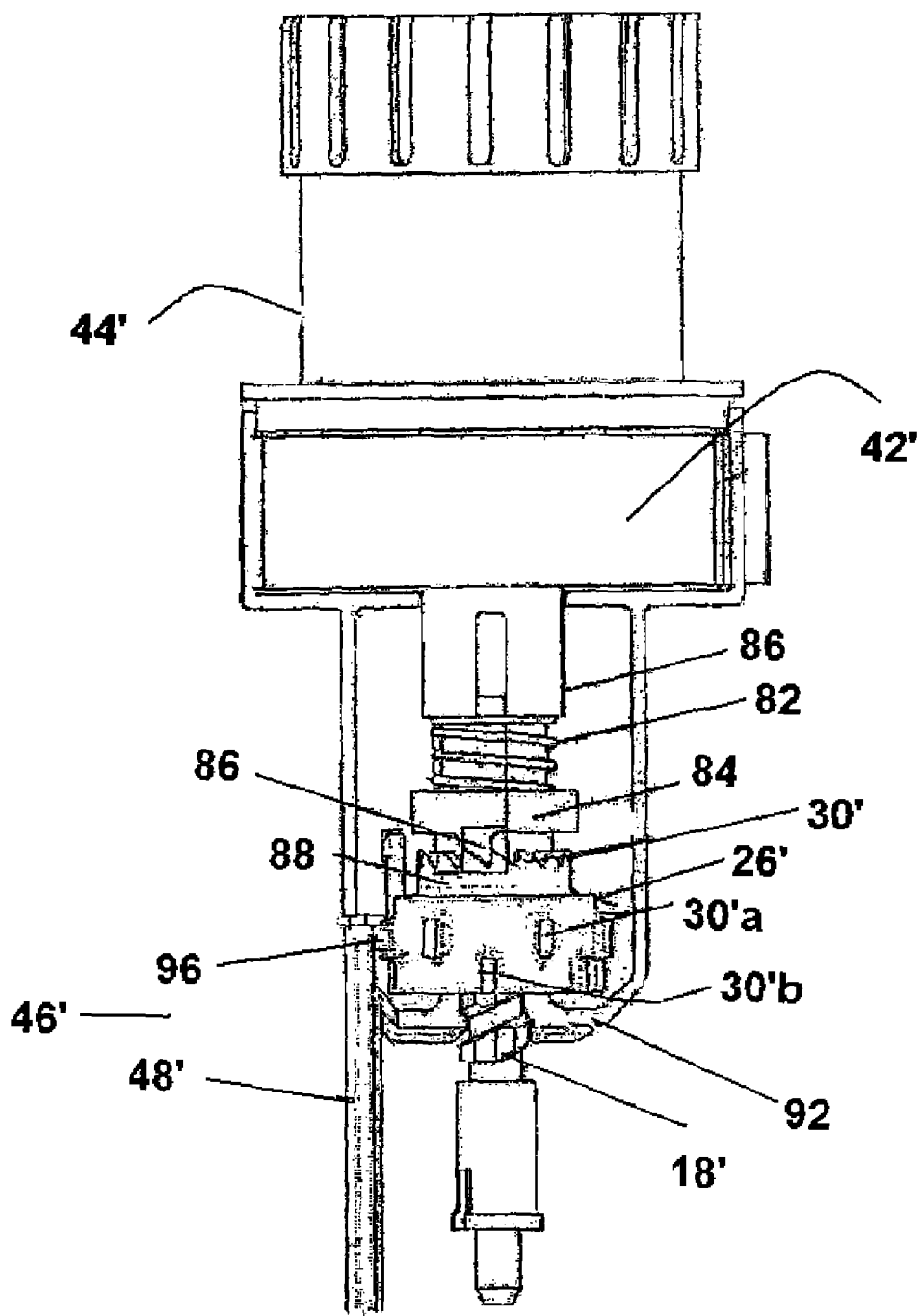

DEVICE FOR DELIVERING MEDICAMENT ENCOMPASSING A PRESSURE RELEASE MECHANISM

TECHNICAL FIELD

The present invention relates to a pressure release mechanism, and in particular in connection with medicament containing devices where the medicament is in a container and is exposed to pressure when the medicament is to be delivered.

BACKGROUND ART

There are numerous devices for delivering medicament on the market and also patented where the medicament is arranged in a container, such as a syringe, cartridge and the like, and wherein the medicament is exposed to pressure when it is to be delivered. A very common design is a generally tubular compartment having a stopper in one end of the compartment and a needle unit attached to the opposite end of the compartment.

In order to deliver a quantity of medicament, the stopper is exposed to pressure, i.e. pushed into the compartment by a pusher rod, which could be done manually by a finger of a physician or trained person, which is the case for simple handheld syringes, or by pressure means such as springs or compressed air cartridges, which is common in automatic or semi-automatic injectors.

In many instances it is desirable to be able to deliver a certain specified quantity of the medicament. This is for example the case with a multi-dose injection device, which is capable of delivering a number of specified, set, doses until the compartment is empty. One example is disclosed in the European patent application No. 05104734.8 where specific doses can be set before injection. The injection device disclosed is arranged with spring means for exerting a pressure on the medicament for delivering a specific dose, i.e. pushing the plunger rod and thus the stopper into the container. The delivery of a dose requires a certain force from the spring means in order to overcome the friction between the somewhat resilient stopper and the inner surface of the container and also to be able to press the medicament in liquid form through a rather small passage in the needle, possibly within a predetermined time.

Due to the elasticity of the components under pressure such as the stopper and also the medicament of non-newtonian, there is a prevailing pressure even when the stopper has been moved a predetermined distance and the dose has been delivered. This is in particular pronounced when handling medicament with rather high viscosity, medicament having resilient properties.

With this type of substance with high viscosity, and because very small needles are often used, a rather large force is required and because of the elasticity of the components, often a certain small quantity of the substance comes out of the needle even after performed injection when the pressure is released, i.e. there is some dripping from the needle, which is unwanted, in particular when treating a patient and the substance may be dripping on the patient's skin, possibly causing irritation or inconvenient, undesirable effects.

The above mentioned gel-based substances are typically injected manually, i.e. a normal type of syringe is used. Because of the rather large forces required for injecting the substances, and also due to the many small injections needed for a treatment, it is tiresome for the operator to use such a syringe during a treatment.

There are thus a number of aspects that are addressed with the present invention.

DISCLOSURE OF INVENTION

The aim of the present invention is to remedy a number of drawbacks and problems associated with the state of the art devices of the above mentioned type and to provide improvements that facilitate the handling of medical devices.

This aim is achieved with a device according to claim 1. Preferable embodiments of the present invention are subject of the dependent claims.

According to a main aspect of the present invention it is characterized by a device for delivering medicament comprising a housing; a container arranged to contain medicament, which container further comprises an opening arranged to expel medicament from the container; pressure means comprising a movable wall part within said container and a pressure member arranged to exert pressure on the medicament inside the container for expelling a certain predetermined quantity of the medicament through the opening; driving means for driving said pressure means; and activation means for activating said driving means wherein said device further comprises pressure release means for releasing the pressure on the medicament after the predetermined dose has been expelled through the opening.

According to another aspect of the invention, said pressure member is arranged to interact with said driving means for moving said movable wall part forwardly and thereby expelling a certain predetermined quantity of the medicament through the opening, and wherein said pressure member is also arranged to interact with said pressure release means for moving said pressure member slightly backwards after the predetermined dose has been expelled through the opening.

The advantages with the present invention are several. The pressure release means ascertains that the residual pressure in the components of the device after delivery of medicament is relieved, which thereby prevents any medicament from being expelled after injection, i.e. preventing drooling of the device.

Many devices comprise pressure means in the form of a plunger rod activated by spring means, which plunger rod moves axially into the compartment of the medicament and the present invention enables the pressure on the plunger rod to be released due to a short axial movement backwards at the end of the injection. With this reliable mechanical solution, no surplus medicament is expelled after injection, which is a particular problem with medicament having a high viscosity or even gel-like properties. However the drooling phenomenon is not limited to such substances but is as relevant for medicament with lower viscosity.

These and other aspects of and advantages with the present invention will become apparent from the following detailed description of the invention and from the accompanying drawings.

BRIEF DESCRIPTION OF DRAWINGS

In the following detailed description of the invention, reference will be made to the accompanying drawings, of which FIG. 5 shows an alternative embodiment of an activation mechanism for the present invention.

DETAILED DESCRIPTION OF THE INVENTION

Figure 1:
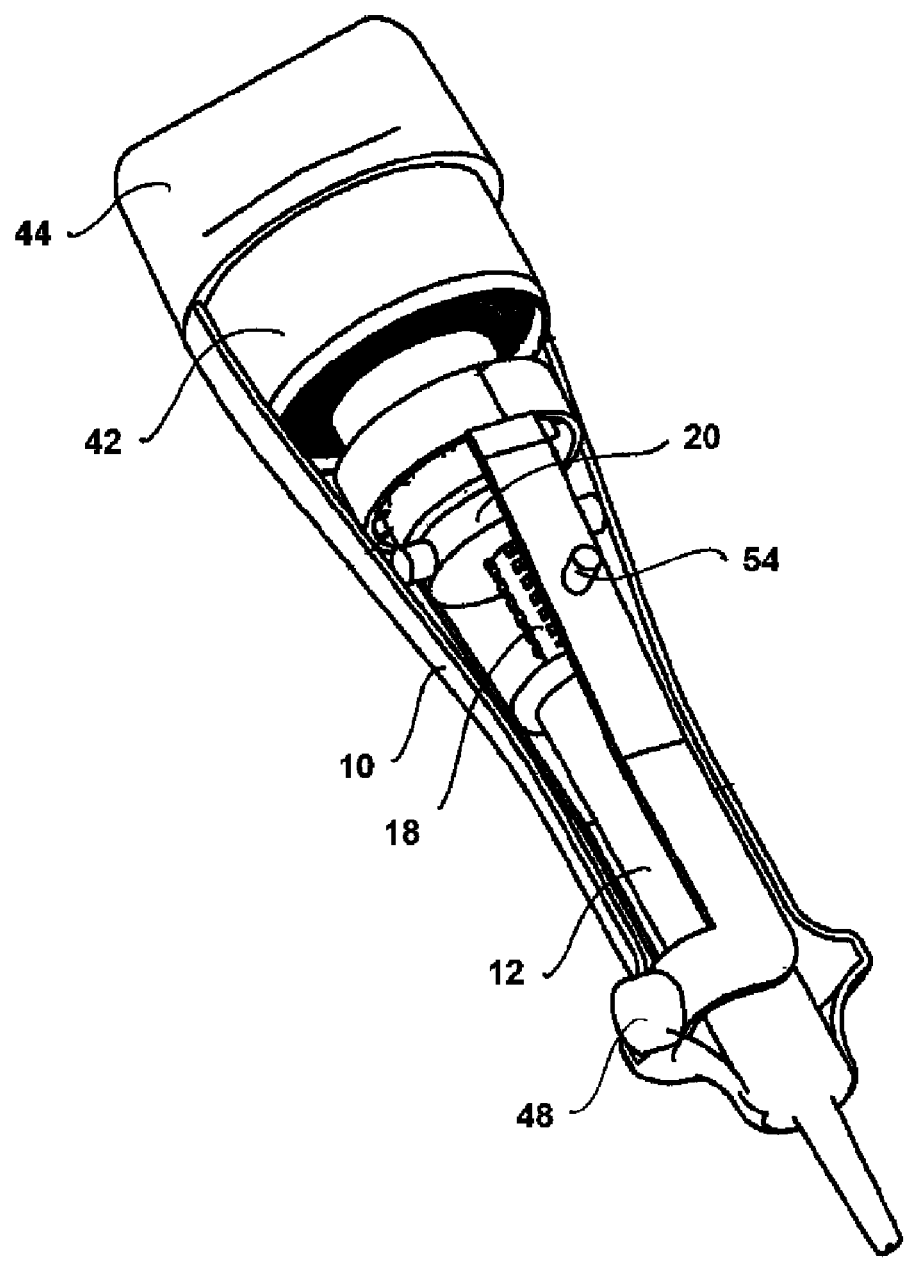
FIG. 1 shows an example of an injection device according to the present invention.

FIG. 1 shows a non-limiting example of a medicament delivery device where the present invention could be utilized. The delivery device comprises a housing 10 designed to be held in one hand for delivering repeated small quantities of medicament step by step. It is however understood that other types of delivery devices may have the pressure release mechanism to be described in detail below.

Figure 2:
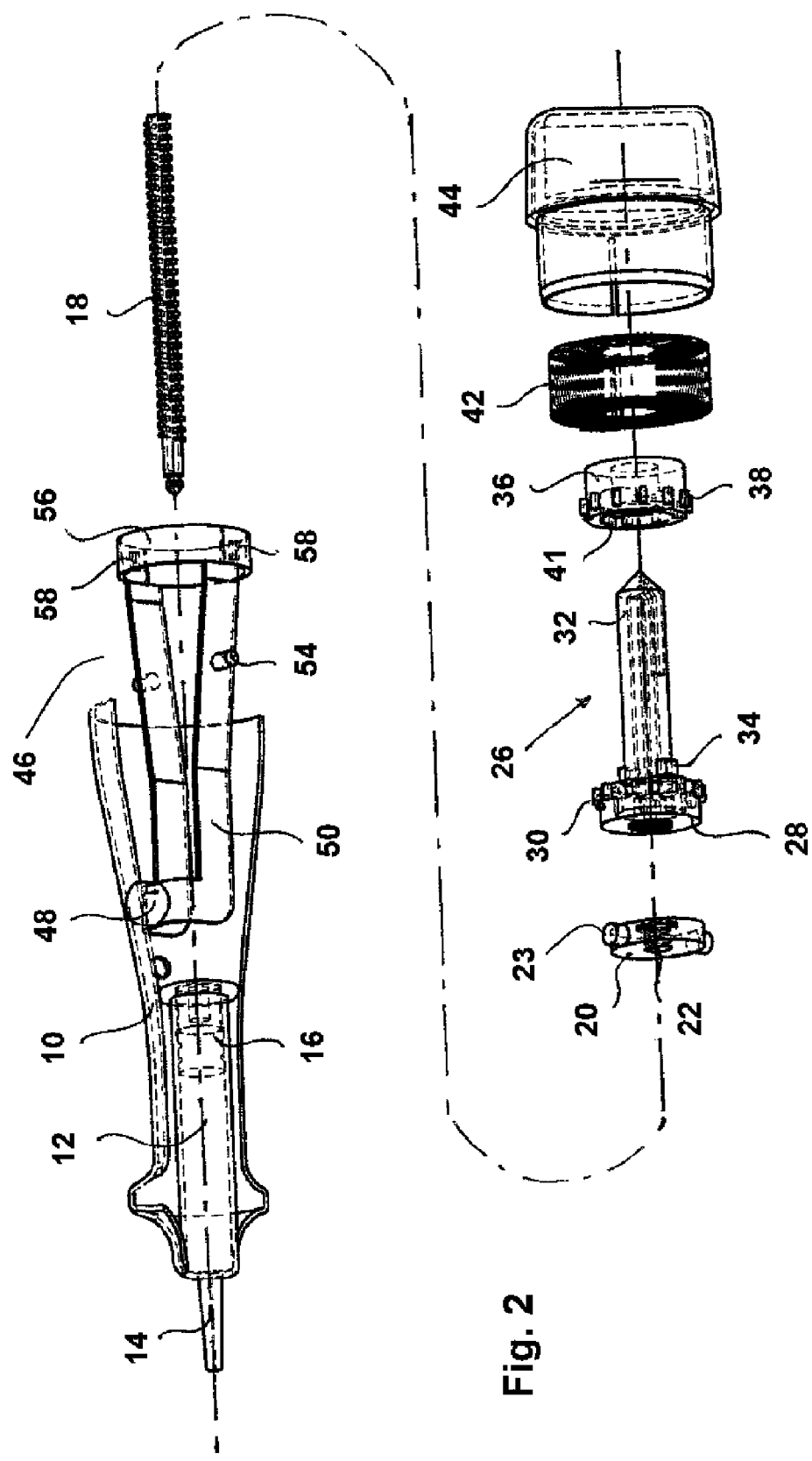
FIG. 2 is an exploded view of the injection device according to FIG. 1, FIG. 3 *a, b* show one embodiment of a pressure release mechanism according to the invention, FIG. 4*a, b* show another embodiment of a pressure release mechanism according to the invention.

As seen in FIG. 2, inside and at the front end of the housing a medicament containing container 12 is arranged having a front end onto which an opening 14 e.g. a needle, may be attached. Said medicament delivery device comprises pressure means including a movable wall part 16, hereafter called stopper, arranged inside the container; and a pressure member 18 as a threaded plunger rod, arranged to push on the stopper. The front end of the plunger rod is preferably pointed to minimize the friction between the plunger rod and the stopper. Said medicament delivery device also comprises driving means including an energy accumulating member 42 and a driver 26.

The Delivery Device of the Present Invention According to a First Embodiment

FIGS. 1, 2, 3a, 3b refer to a configuration of the delivery device wherein the pressure release means comprises a nut 20 having a first mating member 24 arranged and designed to interact with a second mating member 70. Said nut is adapted to be in a non-rotating state but having a forwardly and a backwardly axial movement during medicament delivery due to the interaction with the second mating member 70.

Said nut 20 has a through-going central bore 22 having corresponding threads as the plunger rod, and two outwardly protruding pivoting pins 23 slidable journalled in the housing. As shown in FIGS. 3a and 3b, the upper surface of the nut, facing towards the rear end of the delivery device, is arranged with the first mating member 24 designed and arranged as a number of indentations having a ratchet form, hereafter called the indentations 24. The function of the indentations will be described in detail below.

The driver 26, FIG. 2, is further arranged around the plunger rod. The driver has a lower, cylindrical front portion 28 having a number of outwardly directed protrusions 30 evenly spaced around its circumference where the distance between two adjacent protrusions constitutes a certain predetermined dose quantity, and a second elongated cylindrical portion 32. In the transition between the first and the second portion, two outwardly directed ledges 34 are arranged on opposite sides of the driver. The driver is hollow to accommodate the plunger rod in a rotationally locked position. The front surface of the driver, i.e. facing the front end of the delivery device, is designed to have the second mating member 70 designed and arranged as indentations, hereafter called the indentations 70, that cooperate with the indentations 24 of the nut 20 as a pressure release mechanism that will be described below.

Surrounding the second portion 32 of the driver 26 is a drive wheel 36 of a generally cylindrical shape. The outer surface of the drive wheel is arranged with a number of evenly spaced outwardly directed protrusions 38 having the same increment distance as the protrusions of the driver. The drive wheel is further arranged with a central through-going bore 40 having a diameter slightly larger than the second portion of the driver. The through-going bore is further arranged with cut-outs 41 to accommodate the ledges 34 of the driver 26, but somewhat larger, corresponding to the increment distance of the protrusions, as will be described below, to enable a certain rotational movement between the driver 26 and the drive wheel 36.

Further the energy accumulating member 42 e.g. a flat spring, is wound around the second portion of the driver having its inner end attached to the driver 26. A tensioning knob 44 is arranged at the rear end of the delivery device, to which the outer end of the spring 42 is attached. An activation mechanism 46 is also arranged on the delivery device. It comprises a button 48 protruding through a hole in the housing. The button is attached to a fork-like section having two arms 50 on either side of the container and plunger rod. Two outwardly protruding pivoting pins 54 are arranged on each of the arms, which pivoting pins are slidable and resilient journalled in the housing. On the rear end of the arms, a ring 56 is attached. The inner side of the ring is arranged with oppositely placed, inwardly directed ledges 58. The ledges are positioned 90° in relation to the pivoting pins 54.

The device is intended to function as follows. The needle 14 is attached to the front end of the device and the container by suitable means and a needle sheath is removed. The tensioning knob 44 is then turned whereby the spring 42 is tensioned. The driver is prevented from turning due to that at least one of the ledges 58 of the ring 56 of the activator is in contact with one of the protrusions 30 of the driver.

When an injection is to be performed, the needle is penetrated on a suitable location on the skin, and the button 48 is activated by a backwardly axial movement. The activation of the button causes the ledge 58 of the activator to move out of contact with the protrusion 30 of the driver, whereby the driver is free to rotate. Further, the movement of the activation mechanism causes the opposite ledge 58 to move in contact with the protrusions 38 of the drive wheel 36, thereby locking the drive wheel from rotation.

The rotation of the driver 26 causes the plunger rod 18 to rotate and causes also its indentations 70 to cooperate with the indentations 24 of the nut 20. Due to the threaded engagement between the plunger rod and the nut 20 and the indentations cooperation, the plunger rod moves axially; first forwardly pushing on the stopper 16 whereby the medicament is expelled through the needle and thereafter backwardly to obtain a pressure release on the plunger and thereby on the stopper and on thus the content of the container.

When the driver has rotated a certain increment distance the ledge 34 of the driver 26 comes in contact with a side wall of the cut-outs 41 of the drive wheel 36, and because the drive wheel is locked, the movement of the driver is stopped. In this it is to be understood that the distance between the protrusions of the driver, together with the pitch of the thread of the plunger rod constitutes a certain predetermined dose quantity. I.e. in order to set a specific dose, which is done during manufacture of the device, a certain distance is chosen between the protrusions as well as a certain pitch of the threads of the plunger rod.

When the button 48 is released, the slidable and resilient pivoting pins 54 causes the activation mechanism and thereby one of the ledges 58 to again come in contact with a protrusion 30 of the driver, at the same time as the ledge 58 previously holding the drive wheel 36 moves out of contact with the protrusions 38 of the drive wheel, whereby it is released. A small spring, not shown, is arranged between the driver and the drive wheel to move the drive wheel back to the original position in relation to the driver. The injector is now ready for a subsequent injection.

The Delivery Device of the Present Invention According to a Second Embodiment

FIGS. 1, 2, 4a, 4b refer to a configuration of the delivery device, wherein the pressure release means comprises a nut 20' having a first mating member 24' which is arranged and designed to interact with a second mating member 70' of a ring 60. Said ring 60 is fixedly attached to the inner surface of the housing, and has further a through-going central bore.

As shown in FIGS. 4a and 4b, the upper surface of the ring 60, facing towards the proximal end of the delivery device, is arranged with the second mating member 70' arranged and designed as a number of indentations, hereafter called the indentations 70', having a kind of wavy form "valleys". The function of the indentations 70' will be described in detail below.

The first mating member 24' of the nut 20' is arranged and designed as a number of small wheels, hereafter called the wheels 24'. As shown in FIGS. 4a and 4b, the upper surface of the nut 20', facing towards the distal end of the delivery device, has an elongated cylindrical portion 25 arranged around the plunger rod and having corresponding threads as the plunger rod. Further, said elongated cylindrical portion 25 passes through the through-going central bore of the ring 60 in order to be rotationally connected to the driver 26 (not shown).

At the start of an injection, the wheels 24' are placed in the "valleys" of the ring 60. Thereafter, the rotation of the driver 26 causes both the plunger rod 18' and the nut 20' to rotate wherein the wheels 24' are moved out of the indentations 70' or "valleys" and at the end of the injection, the wheels 24' will move into the next valley. This forwardly and backwardly axial movement of the nut 20' will cause a pressure release on the plunger rod 18' and thereby on the stopper 16 and on thus the content of the container.

Alternative Activation Mechanism

In FIG. 5 is shown a distal part of the medicament delivery device comprising a tensioning knob 44' connected to an energy accumulating member 42' in the form of a flat spiral spring and a threaded plunger rod 18'. Said medicament delivery device shown in FIG. 5 shows also a driver 26', a coupling member 80 and a coupling spring 82, wherein said coupling member further comprising a crown 84 with beveled protrusions 86. The driver 26' is provided with a skirt 88 and beveled recesses 90 as well as a non-rotating bearing 92, provided with an interior tubular formed part (not shown).

The exterior of the proximal part of the driver 26' is provided with a number of dose step protrusions 30', equally distributed along the circumference of the proximal part of the driver 26'. Every other protrusion 30'a is however provided a predetermined distance distal to the rest of the protrusions 30'b. The protrusions 30'a are thus provided equally distributed along the circumference of the driver 26' with their centers provided a certain distance from the proximal end of the driver 26', and the protrusions 30'b are thus also provided equally distributed along the circumference of the driver 26' but with their centers provided a shorter distance from the proximal end of the driver 26' than the protrusions 30'a. The distance between the centers of every protrusion 30' along the circumference of the driver 26' is however equal if, as in this case, the predetermined dose steps are to be equally large, i.e. every dose step delivers the same predetermined amount of medicament.

An activation mechanism 46' of the delivery device according to FIG. 5 is provided with a slidable arm 48' provided with an inwardly protruding stopper means 96 adapted to set the driver 26' in a non-rotating state as well as a rotating state. The activation mechanism 46', and thus also the stopper means 96, is therefore adapted to be moved in the longitudinal direction of the device with a distance that corresponds to the distance between the centers of the protrusions 30'a and 30'b in the longitudinal direction. That is, when the stopper means 96 abuts against, as seen in FIG. 5, the right hand side of a protrusion 30', the driver 26' is prevented to be rotated counterclockwise, i.e. the device is thus in a non-medicament delivery state.

When the delivery device is adapted to be used, the user rotates the tensioning knob 44' clock-wise, preferably the maximum number of steps whereby the spiral spring thus winds up and accumulates the largest permitted energy. If the stopper means abut against a protrusion 30'a provided closer to the distal end of the driver 26' than the protrusions 30'b, the user then moves the activation mechanism 46 and thus also the stopper means 96, the predetermined distance towards the proximal end of the device, whereby the stopper means 96 releases the plunger rod driver 26' for rotation which sets the device in a medicament delivery state. If the stopper means 96 on the other hand abuts against a protrusion 30'b, the user then instead moves the activation mechanism 46' and thus also the stopper means 96, the predetermined distance towards the distal end of the device, whereby the stopper means 96 releases the driver 26' for rotation.

When the driver 26' is free to rotate, the output torque provided by the spring 42' will rotate the driver 26' and hence also the rod 18'. However, independent of the energy accumulated in the spring 42', the driver 26' will only rotate until the stopper means 96 abuts against the protrusion 30' following the protrusion 30' it previously abutted against in the direction along the circumference of the driver 26', whereby the stopper means 96 travels along the circumferential surface of the driver 26' the predetermined distance between the two protrusions 30'a and 30'b in the direction along the circumference of the driver 26', each time the driver is rotated.

That is, if the stopper means 96 initially abuts against the right hand side of the protrusion referred to as 30'a in FIG. 5, the stopper means 96 will after the one step counter clockwise rotation of the driver 26', abut against the protrusion referred to as 30'b. The next time the user wants to deliver a dose, he then moves the activation mechanism and the stopper means the predetermined distance towards the distal end of the device, whereby the driver 26' rotates another step. This medicament delivery procedure can be repeated until the flat spiral spring has unwound and adapted is original non-energy accumulated state, or until the container is emptied. If the former occurs before the container is emptied, the user may naturally wind up the spiral spring once again. It may be that the manufacturer of the device delivers the device with the spiral spring already in a pre-tensed state, whereby the device should be used as a disposable article, i.e. when the spring has unwound it may not be used any further. The amount of medicament corresponding to one dose step is thus determined by the manufacturer of the device.

As mentioned above, the distance between a protrusion 30'a and a protrusion 30'b in the direction along the circumference of the driver 26', will determine the amount of medicament to be delivered. If said distance is equal between every protrusion, the amount of medicament will be identical in every dose step. The manufacturer of the device can, however, produce a device comprising a driver 26' with protrusions 30', in which the distance between the protrusions in the direction along the circumference of the member is not equal everywhere. Thus, said distance can vary in correspondence with a predetermined pattern giving rise to a predetermined dose step pattern. For instance, the distance between the protrusions in the direction along the circumference of the driver can become larger and larger, whereupon the amount of medicament delivered will increase for every dose step until the plunger rod driver has completed a full turn.

It is to be understood that the embodiments described above and shown on the drawings are to be regarded only as non-limiting examples of the invention and that it can be modified in many ways within the scope of the patent claims.

The invention claimed is:

1. A device for delivering medicament, comprising:
a housing;
a container which is arranged to contain medicament and includes an opening arranged to expel medicament from the container;
a pressure mechanism comprising a movable wall part within the container and a pressure member arranged to exert pressure on the medicament inside the container for expelling a predetermined quantity of the medicament through the opening;
a driver mechanism arranged to drive the pressure mechanism;
an activation mechanism arranged to activate the driver mechanism; and
a pressure release mechanism interactively connected to the pressure member, wherein the pressure release mechanism comprises a first mating member arranged to interact with a second mating member so as to release the pressure on the medicament only after the predetermined dose has been expelled through the opening.

2. The device of claim 1, wherein the pressure member is arranged to interact with the driver mechanism for moving the movable wall part forwardly and thereby expelling the predetermined quantity of the medicament through the opening, and to interact with the pressure release mechanism for moving the pressure member slightly backwards after the predetermined dose has been expelled through the opening.

3. The device of claim 2, wherein the driver mechanism comprises a driver having the second mating member and being arranged around the pressure member in a rotationally locked position.

4. The device of claim 3, wherein the second mating member is arranged to be rotatable in relation to the first mating member.

5. The device of claim 2, further comprising a ring having the second mating member and being fixedly attached to the inner surface of the housing.

6. The device of claim 5, wherein the first mating member is arranged to be rotatable in relation the second mating member.

7. The device of claim 1, wherein mating surfaces of the two mating members have a ratchet form.

8. The device of claim 1, wherein mating surfaces of the mating members have a wavy form.

9. The device of claim 1, wherein the driver mechanism comprises an energy accumulating member.

10. The device of claim 9, wherein the energy accumulating member is a flat spiral spring.

11. The device of claim 1, wherein the activation mechanism is arranged to interact with the driver mechanism and accordingly deliver the predetermined quantity of medicament step by step.

* * * * *